(12) United States Patent
Cantatore et al.

(10) Patent No.: US 7,300,281 B2
(45) Date of Patent: Nov. 27, 2007

(54) ENDODONTIC FILE HAVING BI-DIRECTIONAL SCRAPING EDGES

(76) Inventors: Giuseppe Cantatore, 62, Via Della Luce, Rome (IT) 00153; Arnaldo Castellucci, Via Palestro, 3, Florence (IT) 50123; Elio Vincenzo Giovanni Berutti, Via Servais 140-17, Turin (IT) 10146

( * ) Notice: Subject to any disclaimer, the term of this patent is extended or adjusted under 35 U.S.C. 154(b) by 86 days.

(21) Appl. No.: 11/195,100

(22) Filed: Aug. 2, 2005

(65) Prior Publication Data
US 2007/0031783 A1    Feb. 8, 2007

(51) Int. Cl.
*A61C 5/02* (2006.01)
(52) U.S. Cl. .................................................... 433/102
(58) Field of Classification Search ................ 433/102, 433/81, 224, 165–166
See application file for complete search history.

(56) References Cited

U.S. PATENT DOCUMENTS

| | | | |
|---|---|---|---|
| 4,443,193 A | 4/1984 | Roane | |
| 4,536,159 A | 8/1985 | Roane | |
| 4,934,934 A | 6/1990 | Arpaio, Jr. et al. | |
| RE34,439 E | 11/1993 | Heath | |
| 5,380,200 A | 1/1995 | Heath et al. | |
| 5,464,362 A | 11/1995 | Heath et al. | |
| 5,658,145 A | 8/1997 | Maillefer et al. | |
| 5,692,902 A | 12/1997 | Aeby | |
| 5,735,689 A * | 4/1998 | McSpadden | 433/102 |
| 5,762,497 A * | 6/1998 | Heath | 433/102 |
| 5,873,719 A | 2/1999 | Calas et al. | |
| 5,897,316 A | 4/1999 | Buchanan | |
| 5,921,775 A | 7/1999 | Buchanan | |
| 5,941,760 A | 8/1999 | Heath et al. | |
| 5,975,899 A | 11/1999 | Badoz et al. | |
| 6,012,921 A | 1/2000 | Riitano | |
| 6,042,376 A | 3/2000 | Cohen et al. | |
| 6,074,209 A | 6/2000 | Johnson | |
| 6,106,296 A * | 8/2000 | Johnson | 433/224 |
| 6,217,335 B1 | 4/2001 | Riitano et al. | |
| 6,267,592 B1 | 7/2001 | Mays | |
| 6,312,261 B1 | 11/2001 | Mays | |
| 6,315,558 B1 | 11/2001 | Farzin-Nia et al. | |

(Continued)

FOREIGN PATENT DOCUMENTS

EP    1236441    9/2002

(Continued)

OTHER PUBLICATIONS

Search Report, Nov. 15, 2006, European Patent.

*Primary Examiner*—John J Wilson
(74) *Attorney, Agent, or Firm*—Gable Gotwals

(57) ABSTRACT

An endodontic file having an elongated shank with a proximal end portion, a distal end and a tapered working portion extending from the proximal portion to the distal end, the external surface of the shank working portion being defined in part by a plurality of at least two equally spaced apart continuous helical flutes formed into a central core portion of the shank working portion, the flutes having therebetween an equal number of spiraled spaced apart flanges, each flange having a semi-circular surface having a leading edge and a trailing edge, each edge being in or parallel to a plane of the shank longitudinal axis, each leading and trailing edges providing a cutting or scraping edge.

13 Claims, 2 Drawing Sheets

U.S. PATENT DOCUMENTS

| | | |
|---|---|---|
| 6,390,819 B2 | 5/2002 | Riitano |
| 6,419,488 B1 | 7/2002 | McSpadden et al. |
| 6,514,076 B1 | 2/2003 | Bleiweiss et al. |
| 6,520,774 B1 | 2/2003 | Mays |
| 6,644,972 B1 | 11/2003 | Mays |
| 6,746,245 B2 | 6/2004 | Riitano et al. |
| 2002/0090594 A1 | 7/2002 | Riitano et al. |
| 2003/0013067 A1 | 1/2003 | Bleiweiss et al. |
| 2003/0077553 A1 | 4/2003 | Brock |
| 2004/0023186 A1 | 2/2004 | McSpadden |
| 2004/0043357 A1 | 3/2004 | Garman |
| 2004/0058297 A1 | 3/2004 | Danger |
| 2004/0121283 A1* | 6/2004 | Mason ................ 433/102 |
| 2004/0191723 A1 | 9/2004 | Shearer et al. |

FOREIGN PATENT DOCUMENTS

| | | |
|---|---|---|
| EP | 1634535 | 3/2006 |

\* cited by examiner

ENDODONTIC FILE HAVING BI-DIRECTIONAL SCRAPING EDGES

REFERENCE TO PENDING APPLICATIONS

This application is not related to any pending domestic or international patent applications.

REFERENCE TO MICROFICHE APPENDIX

This application is not referenced in any microfiche appendix.

BACKGROUND OF THE INVENTION

1. Field of the Invention

This invention relates to a flexible tool that is particularly adaptable for use as an endodontic instrument, most particularly, an endodontic file for use by practitioners in removing the pulpal material from an exposed root of a tooth and for shaping the root canal to receive filler material, usually gutta-percha.

2. Background of the Invention

One of the most significant advancements in dentistry in recent years has been improved treatment of abscessed teeth. In the past a tooth, once abscessed, was usually pulled as the only remedy for alleviating the intense pain. By "abscessed" usually means that the root canal of the tooth becomes infected and the infection causes pressure on the tooth and the nerve endings associated therewith that result in, sometimes, almost unbearable pain. With the advent of endodontics the drastic measure of extracting a tooth that had become abscessed has been eliminated.

The first step in the endodontic treatment of an abscessed tooth is to drill an opening in the crown of the tooth to provide access to the root canal. Once the root canal is exposed, the practitioner then must thoroughly clean the root canal of pulpal material since if the pulpal material is not thoroughly and carefully removed it can be the source of continued infection. Not only is it necessary that the pulpal material be removed but the root canal usually must be shaped in such a way as to permit filling of the root canal with a filler material. While other types of filler materials have been provided still at the present time the most common filler is a paste-like material referred to as "gutta-percha." If the canal is not properly cleaned and shaped the step of filling with gutta-percha may leave void areas that invite the introduction into the root canal of organic matter that can be followed by bacterial action. For these reasons much of the effort of a practitioner to successfully accomplish the endodontic treatment of an abscessed tooth is the cleaning and shaping of the root canal. These steps are accomplished utilizing small diameter tapered files that are inserted by the practitioner through the exposed crown area into the root canal. The canal must be cleaned from the crownal area advancing to the root apex.

A root canal is typically in a tapered configuration, that is, the cross-sectional area of canals is usually greater near the crown of the tooth and is at a minimum at the apex of the tooth, that is, the distal end of the root canal. While the root canal is naturally tapered it is not tapered symmetrically and the canal can have inclusions in intermediate portions between the apex and the crown area that interfere with the passage of filler material. Therefore the root canal must be shaped to remove unnecessary intrusions and to improve the chances that the practitioner can successfully fill the root canal.

Files are usually provided with a small cylindrical plastic handle portion by which the practitioner manually manipulates the files. By "manipulation" means inserting a file into a canal and reciprocating it to file away intrusions and at the same time to remove pulpal material. Typically the practitioner inserts a file to the point of resistance and then rotates and reciprocates the file to engage spiral scraping edges with the canal wall. The file is then extracted to remove pulpal material and matter scraped from the wall. This procedure is repeated as necessary to clean the entire length of the canal. In the cleaning process the practitioner usually starts with a file of a small diameter and then, as progress is made in cleaning the canal, larger diameter files are employed until the root canal is shaped and cleaned to the apex. Accordingly, endodontic files usually come in sets of standard tapers and varying from smaller to larger diameters.

Instead of manually rotating an endodontic file the practitioner may insert the file proximal end into the chuck of a hand piece by which the file is mechanically rotated.

Root canals are characteristically not straight. Some root canals curve more than others but few are perfectly straight from the crown to the apex. Therefore it is important that files be flexible so as to be able to follow the natural curvature of the root canal as it is cleaned and shaped from the tooth crown to the tooth apex. If a file is too stiff it can result in the file protruding through a side wall of a tooth root which can introduce an avenue of infection into the tooth. Further, if the file is stiff it is less successful in cleaning the entire area of a canal since the stiffness will cause the file to be deflected drastically to one side of a curve in a canal leaving a portion of the wall that defines the curve unexposed to the action of the file. Therefore, a high degree of flexibility is a desirable characteristic of an endodontic file.

In addition, the strength of a file is very important. In the process of reciprocating and rotating a file in a tooth it is possible for the file to break, leaving a broken part in the tooth. This creates a serious problem for the practitioner. Accordingly, it has long been a desire of the dental profession to have available dental files that are highly flexible and yet strong to resist separation as a result of a torsional twist or pulling action as a file is manipulated within a root canal. The present invention provides a way of substantially increasing the flexibility of dental files while at the same time increasing resistance against torsional or elongational separation.

Further, most endodontic files function only in one direction of rotation instead in both directions of rotation. Unidirectional files result in reduced efficiency.

3. Description of the Prior Art

For background information relating to the subject matter of this invention and specifically relating to dental reamer/files, reference may be had to the following issued United States patents and publications:

| PATENT NUMBER | INVENTOR(S) | ISSUE DATE | TITLE |
| --- | --- | --- | --- |
| 4,443,193 | Roane | 04/17/1984 | Endodontic Instrument |
| 4,536,159 | Roane | 08/20/1985 | Endodontic Instrument |
| 4,934,934 | Arpaio, Jr. et al. | 06/19/1990 | Dental File/Reamer Instrument |

-continued

| PATENT NUMBER | INVENTOR(S) | ISSUE DATE | TITLE |
| --- | --- | --- | --- |
| 5,380,200 | Heath et al. | 01/10/1995 | Endodontic Instrument Of Predetermined Flexibility |
| 5,464,362 | Heath et al. | 11/07/1995 | Endodontic Instrument |
| 5,658,145 | Maillefer et al. | 08/19/1997 | Set Of Instruments For Boring Dental Radicular Canals And Method Therefor |
| 5,692,902 | Aeby | 12/02/1997 | Set Of Instruments For The Boring Of Radicular Dental Canals |
| 5,873,719 | Calas et al. | 02/23/1999 | Dental Reamer |
| 5,897,316 | Buchanan | 04/27/1999 | Endodontic Treatment System |
| 5,921,775 | Buchanan | 07/13/1999 | Endodontic Treatment System |
| 5,975,899 | Badoz et al. | 11/02/1999 | Dental Reamer |
| 6,012,921 | Riitano | 01/11/2000 | Endodontic Systems For The Anatomical, Sectional And Progressive Corono-Apical Preparation Of Root Canals With Three Sets Of Dedicated Instruments |
| 6,074,209 | Johnson | 06/13/2000 | Reduced Torque Endodontic File |
| 6,217,335 | Riitano et al. | 04/17/2001 | Endodontic Systems And Methods For The Anatomicall, Sectional And Progressive Corono-Apical Preparation Of Root Canals With Minimal Apical Intrusion |
| 6,267,592 | Mays | 07/31/2001 | Highly Flexible Instrument For Dental Applications |
| 6,312,261 | Mays | 11/06/2001 | Endodontic Obturator With Removable Carrier And Method Of Use Thereof |
| 6,315,558 | Farzin-Nia et al. | 11/13/2001 | Method Of Manufacturing Superelastic Endodontic Files And Files Made Therefrom |
| 6,390,819 | Riitano | 05/21/2002 | Endodontic Systems And Methods For The Anatomical, Sectional And Progressive Corono-Apical Preparation Of Root Canals With Dedicated Stainless Steel Instruments And Dedicated Nickel/Titanium Instruments |
| 6,419,488 | McSpadden et al. | 07/16/2002 | Endodontic Instrument Having A Chisel Tip |
| 6,514,076 | Bleiweiss et al. | 02/04/2003 | Precipitation Hardenable Stainless Steel Endodontic Instruments And Methods For Manufacturing And Using The Instruments |
| 6,520,774 | Mays | 02/18/2003 | Highly Flexible Instrument For Medical Applications |
| 6,644,972 | Mays | 11/11/2003 | Endodontic Obturator With Removable Carrier And Method Of Use Thereof |
| 6,746,245 | Riitano et al. | 06/08/2004 | Methods For Cleaning And Shaping Asymmetrical Root Canals In An Anatomical Fashion |
| 2004/0121283 | Mason | 06/24/2004 | Precision Cast Dental Instrument |
| 2003/0077553 | Brock | 04/24/2003 | Endodontic Instrument Having Notched Cutting Surfaces |
| 2004/0058297 | Danger | 03/02/2004 | Root Canal Instrument |
| 2004/0043357 | Garman | 03/04/2004 | Endodontic Instrument |
| 2004/0023186 | McSpadden | 02/05/2004 | Multi-Tapered Endodontic File |
| 2003/0013067 | Bleiweiss et al. | 01/16/2003 | Precipitation Hardenable Stainless Steel Endodontic Instruments And Methods For Manufacturing And Using The Instruments |
| Re. 34,439 | Heath | 11/09/1993 | Dental Compactor Instrument |

BRIEF SUMMARY OF THE INVENTION

The invention herein is a dental reamer/file that is for use in performing endodontic procedures, that is, specifically, cleaning and shaping the root canal of a tooth to prepare the tooth to receive a filler material, such as gutta percha.

The invention is specifically a file which may be manipulated manually or by machine, that is, a hand piece that is commonly used by endodontic practitioners. The file includes an elongated shank with a proximal end, a distal end and a tapered working portion that extends from the proximal portion to the distal end. The shank also includes either an enlarged diameter handle portion, typically made of plastic for manually manipulating the file or a smaller diameter metal portion, usually integral with the file, that is configured to be received in a dental hand piece by which the file is mechanically rotated and can be manipulated by the practitioner.

The external surface of a shank working portion is defined by a plurality of at least two spaced apart continuous helical flutes. These helical flutes are formed into a central core portion of the shank. The flutes have therebetween an equal number of spiraled, spaced apart flanges. Each flange has a semi-circular surface having a leading edge and a trailing edge. Each edge is essentially in or parallel to a plane of a shank longitudinal axis. Each leading edge and trailing edge provides a cutting/scraping edge, that is, each edge provides a surface for reaming or filing the root canal in which the file is employed. "Reaming" typically means that the edge has a neutral rake angle, that is, a rake angle that does not tend to cut into the root canal surface but that scrapes away any protruding material in the root canal.

The file can be configured so that each edge is a cutting edge, that has a negative rake angle so that each edge tends to cut into the surface of the root canal. Since the opposed edges of each flange are for scraping or cutting, the file is bi-directional. By this it is meant that as the file is rotated in a clockwise direction the leading edges of the shank spiral portions ream or cut into the surface of the root canal and if the file is rotated in the reverse direction, then that which was initially a trailing edge becomes a leading edge and the file functions to ream or cut the root canal. By providing a file that functions in either forward or reverse directions of rotation the user can more quickly, expeditiously and efficiently clean and shape a root canal as a part of an endodontic procedure.

A more complete understanding of the invention will be obtained from the following detailed description of the preferred embodiments and claims, taken in conjunction with the attached drawings.

BRIEF DESCRIPTION OF THE DRAWINGS

FIG. 2 shows a cross-sectional view wherein the spiral flanges forming a part of the external surface of the shank working portion of the file have cutting edges that extend at a radius from the axis of rotation of the file. That is, where each edge is formed by a surface that intersects a circumference of the file at a 90° angle. FIG. 2 thus illustrates the arrangement wherein the shank edges are at a neutral rake angle.

In FIG. 3 the arcuate surface that defines the spiral helical flanges is of a diameter greater than the diameter of the file itself. In the arrangement of FIG. 3 the edges define a sharper surface for increased scraping or cutting action. FIG. 3 shows the arrangement wherein the edges are at a negative angle with respect to a plane drawn through the longitudinal axis of the file to provide cutting edges that tend to cut into the surface of a root canal.

In FIG. 4 the file edges are at a positive 5° meaning that the edges are not configured to cut but to ream the interior surface of the root canal.

FIG. 5 is substantially similar to FIG. 4 except that the rake angle is a positive 10° illustrating that the rake angle, whether positive or negative, can vary according to the design selected by the manufacturer of the file.

DETAILED DESCRIPTION OF THE PREFERRED EMBODIMENTS

Figure 1:
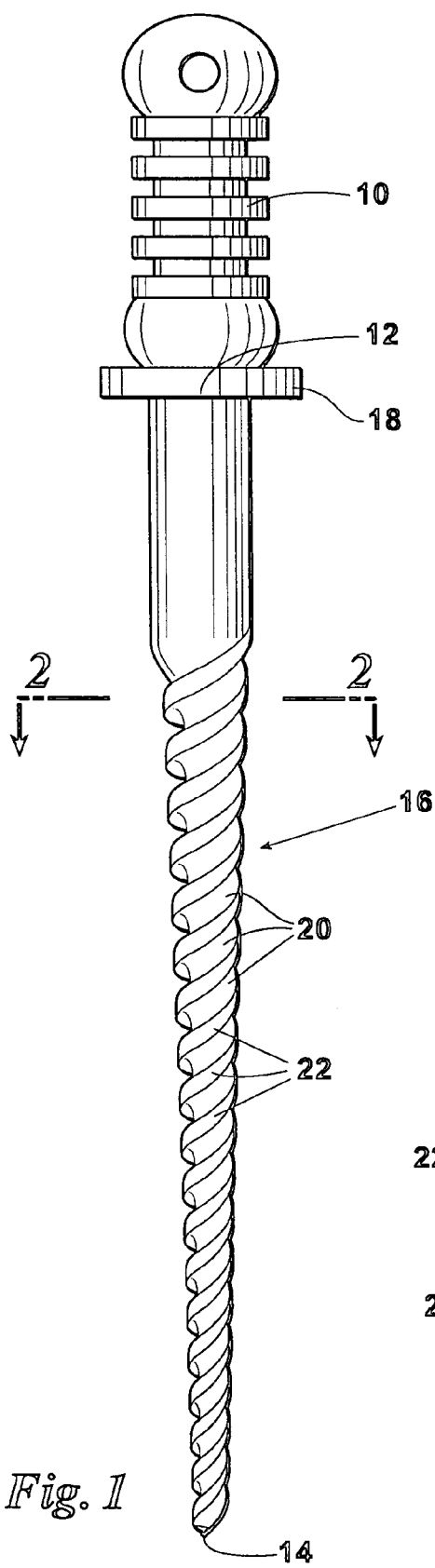
FIG. 1 is an elevational view of an endodontic file of the type that can be used to incorporate the principles of this invention. The file illustrated in FIG. 1 is of the type for manual manipulation, that is, it is the type of file having a small handle at the proximal end that is dimensioned to be engaged between the thumb and forefinger of the practitioner so that the file can be rotated. In the present invention, the file functions either in the forward or reverse direction of rotation to scrape and clean a root canal.

It is to be understood that the invention that is now to be described is not limited in its application to the details of the construction and arrangement of parts illustrated in the accompanying drawings. The invention is capable of other embodiments and of being practiced or carried out in a variety of ways. The phraseology and terminology employed herein are for purposes of description and not limitation.

Elements illustrated in the drawings are identified by the following numbers:

| | |
|---|---|
| 10 | Handle portion |
| 12 | Proximal end |
| 14 | Distal end |
| 16 | Shank portion |
| 18 | Washer |
| 20 | Helical flutes |
| 22 | Helical flanges |
| 24 | Base surface of flutes |
| 26 | Flange external surface |
| 28 | Scraping/cutting edges |
| 30 | Axis of rotation |

Referring to the drawings and first to FIG. 1, an elevational view illustrates generally a typical endodontic file. The file includes a handle portion 10 that is at a proximal end 12 of the file. A distal end 14 is of a substantially reduced diameter compared to the proximal end 12. Intermediate the proximal end 12 and distal end 14 is an elongated shank portion generally indicated by the numeral 16.

Handle portion 10 is typically formed of plastic and is of increased diameter and usually includes a surface configured to be easy to grasp and in which slippage is reduced. Handle portion 10 is illustrated as being typical and the particular shape or configuration of it is not an important part of the present invention.

Slidably received on the shank portion 16 and illustrated as being adjacent handle 10 is an elastomeric washer 18 that is used by the practitioner to mark the depth of penetration of the shank portion 16 into the root canal. As the file is worked into the root canal the practitioner can move washer 18 down against the crown of the tooth and thereby have an accurate indication of the depth that the file has penetrated into the root canal. Washer 18 is prior art and is not a critical part of the present invention.

Figure 2:
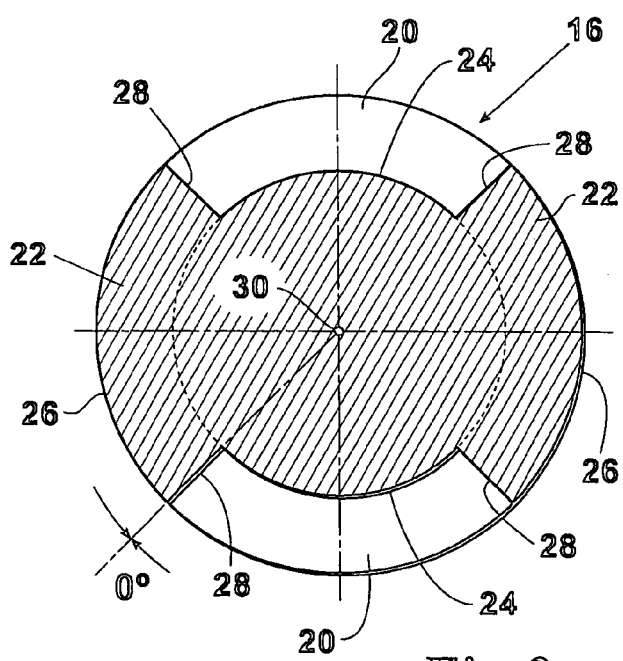
FIG. 2 is a cross-sectional view taken along the line 2-2 of FIG. 1.

Instead, the invention herein is in the configuration of shank portion 16. FIG. 2 is a cross-sectional view taken along the line 2-2 of shank portion 16. As shown in FIG. 1, the shank portion 16 is tapered from a larger basic diameter at the proximal end 12 to a substantially reduced diameter at distal end 14, and distal end 14 is typically pointed as shown. The arrangement of the taper of the shank portion 16 can vary considerably. The taper of the shank portion beginning with the smallest diameter at or adjacent the distal end 14 and ending with the largest diameter at or adjacent the proximal end 12 can vary in many ways. A number of patents exist on the way this taper is arranged. However, the taper itself is not a part of the present invention and the invention herein can be practiced with various taper arrangements. Further, endodontic files are frequently manufactured, sold and used as sets of files in which the diameters vary. In a typical set, the diameters at the proximal end 12 can start with a relatively small diameter and sequentially increase geometrically to a larger diameter. In this way, a practitioner can have available a set of files to gradually expand the diameter of the root canal. Here again, the arrangement of the diameters of the file that is used to practice the invention is not relevant to the present concept. Instead, the invention herein is in the configuration of the external surface of the shank portion 16.

In the present invention the external surface of shank portion 16 is defined by a plurality of at least two equally spaced apart continuous helical flutes 20. These helical flutes extend from the proximal to the distal end and the depth of flutes 20 can vary. In one arrangement, the depth of flutes 20 varies in proportion to the diameter of the shank 16 so that the flutes adjacent proximal end 12 are deeper than the flutes adjacent distal end 14. In the illustrated arrangement there are two continuous spiral flutes 20 as seen in FIG. 2. This is optional as there can be more than two paralleled spiraled flutes. In some designs, three flutes can be employed or even four paralleled flutes. However, for practical reasons, the typical file will have either two or three paralleled flutes. The embodiment herein shows the use of two paralleled flutes 20.

Figure 3:
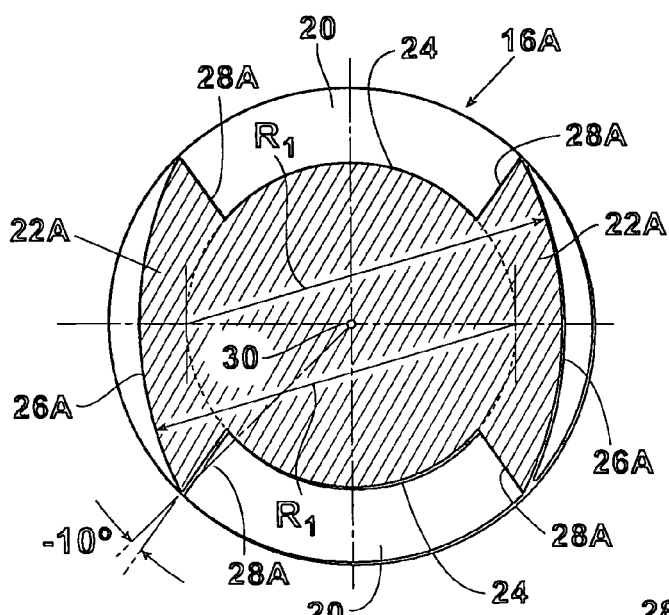
FIG. 3 is a cross-sectional view as shown in FIG. 2 but showing an alternate embodiment of the invention.
Figure 4:
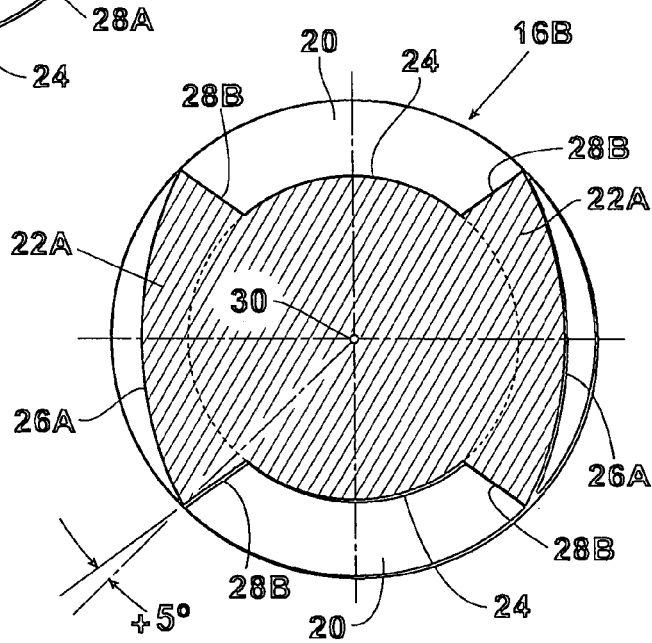
FIG. 4 is a cross-sectional view as shown in FIG. 2 showing an alternate embodiment wherein the flanges have an external surface of increased diameter compared to the file diameter as in FIG. 3.
Figure 5:
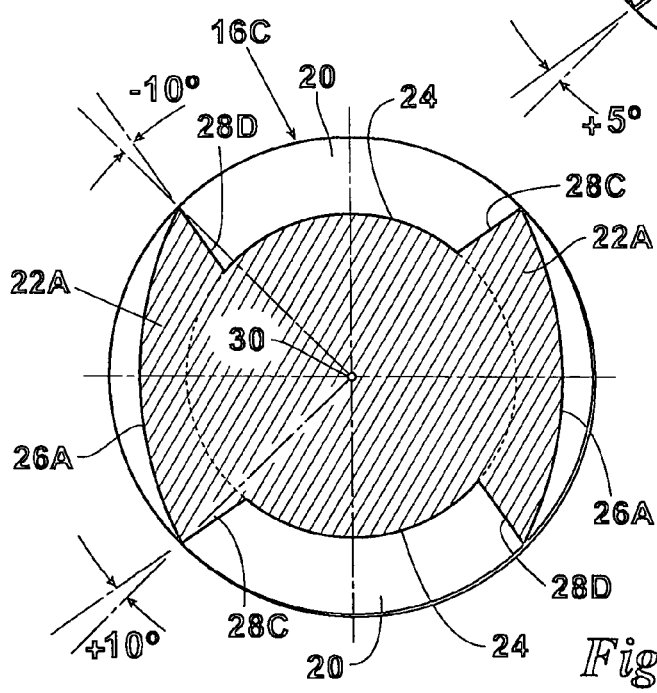
FIG. 5 is a cross-sectional view like FIGS. 2, 3 and 4.

Positioned between helical flutes 20 are helical flanges 22, indicated as 22A and 22B in FIGS. 3-5. Helical flutes 20 each have a base surface 24. Each helical flange 22 has an external surface 26 that is of the full diameter of the cross-sectional area of shank portion 16. In the illustrated arrangement of FIG. 2 the base surface 24 of each of the flutes 20 is semi-circular and in like manner, the external surface 26 of each of the flanges 22 is semi-circular.

The transition between flutes 20 and flanges 22 provide cutting/scraping edges 28. Shank portion 16 has an axis of rotation 30 as seen in FIGS. 2 through 5. In the embodiment shown by the cross-sectional view of FIG. 2, the base surfaces 24 of each of the helical flutes 20 are semi-circular about axis 30 and in like manner, the external surface 26 of each of the spiral flanges 22 is semi-circular about axis 30.

The arrangement of FIG. 2 shows, as previously stated, a rake angle of 0° meaning that the edges 28 are neither fully cutting edges nor fully scraping edges but function somewhat in between.

FIGS. 3 through 5 are cross-sectional views like FIG. 2 but show different embodiments of the invention.

Referring first to FIG. 3, the helical flutes 20 have base surfaces 24 of the same semi-circular shape and diameter as shown in FIG. 2, however, each flange external surfaces 26A is different than in FIG. 2. In the embodiment of FIG. 3 the radius $R_1$ of each flange external surfaces 26A is greater than the radius of the external rotational circumference of the shank portion 16A and the cutting/scraping edges 28A are at a sharper angle. That is, in FIG. 3 the angle of each of the cutting/scraping edges 28A is in a plane that is offset relative to a plane of axis 30. Specifically, in the illustrated arrangement of FIG. 3, the plane of each of the cutting/scraping edges 28A is at an angle of 10° relative to a plane of the shank axis of rotation 30. In this way cutting/scraping edges 28A tend to cut into the surface of the root canal and tend to more rapidly enlarge the internal diameter of the root canal and this is true irrespective of the direction of rotation of the tool.

FIG. 4 is an additional cross-sectional view that is substantially identical to the cross-sectional view of FIG. 3 except that in FIG. 4 the cutting/scraping edges 28B are at a positive 5° angle relative to a plane that extends through the rotational axis 30 which is the same way as saying that the cutting/scraping edges 28B are in planes of +5° relative to a radius of the shank portion 16B.

FIG. 5 is like FIG. 4 except the cutting edges 28C are in a plane that are at a +10° angle relative to a plane that passes through axis of rotation 30. Thus it can be seen by comparing FIG. 3 with FIG. 5 that FIG. 3 has a negative rake angle of 10° that provides a positive cutting action wherein FIG. 5 has a positive rake angle of 10° that provides a negative cutting action, that is, that provides a scraping action rather than a cutting action.

A unique characteristic of the configuration of endodontic file of the disclosure is the provision of a tool that cuts or scrapes when rotated in one direction, that is, as an example, when rotating clockwise and provides a similar cutting or scraping action when rotated in the opposite direction. The file can be manufactured so that in clockwise rotation each leading edge has a negative rake angle and the opposite, or counterclockwise direction, each leading edge has a positive rake angle. In this way the file is arranged so that when rotated clockwise it tends to cut into the root canal but when rotated counterclockwise it tends to scrape the root canal. Contrarily, a file having the same dimensions could be arranged to scrape when rotated in the clockwise direction, that is, the rake angle of the cutting/scraping edges 28 can be positive in one direction and negative in the other direction. Since the flanges 22 are helical, that is, spiraled from the proximal end 12 to the distal end 14, there will be a tendency when a file is rotated in the direction of the spiral to thread or screw the file into the root canal whereas when rotated in the opposite direction, to unthread or screw the file out of the root canal. In this way, by the unique characteristic of the present invention, the file can be arranged to have a positive rake angle when rotated clockwise, that is, in the direction that would tend to thread the file into the root canal and have a negative rake angle when rotated counterclockwise, that is the direction tending to extract it from the root canal. By providing a scraping action when the file tends to thread into the root canal and a cutting action when the file tends to unthread from the root canal the possibility of the file becoming locked into the root canal, and thus the possibility of file breakage, is decreased while at the same time the file provides provision for both scraping and cutting action.

While the invention has been described with a certain degree of particularity, it is manifest that many changes may be made in the details of construction and the arrangement of components without departing from the spirit and scope of this disclosure. It is understood that the invention is not limited to the embodiments set forth herein for purposes of exemplification, but is to be limited only by the scope of the attached claim or claims, including the full range of equivalency to which each element thereof is entitled.

What is claimed is:

1. A dental reamer or file comprising:

an elongated tapered shank having a rotational axis, having a proximal end portion, a distal end and a tapered working portion extending from said proximal portion to said distal end;

the external surface of said shank working portion being defined in part by a plurality of at least two equally spaced apart continuous helical flutes formed into a central core portion of said shank working portion, each flute having a semi-circular recessed depth base surface concentric with said rotational axis and providing resistance to torque breakage, the flutes having therebetween an equal number of spiraled spaced apart flanges, each flange having in a plane perpendicular to the length of said shaft, a semi-circular surface having a leading edge and a spaced apart trailing edge, each leading and trailing edge being essentially in or parallel to a plane of the said shank working portion longitudinal axis, each said leading edge providing a cutting or scraping edge.

2. A dental reamer or file according to claim 1 wherein each said leading edge is at a negative angle relative to a plane of said longitudinal axis providing a positive cutting edge.

3. A dental reamer or file according to claim 1 wherein each said leading edge is at a positive angle relative to a plane of said longitudinal axis providing a negative scraping edge.

4. A dental reamer or file according to claim 1 wherein each said leading edge is at a neutral angle relative to a plane of said longitudinal axis providing a neutral cutting or scraping edge.

5. A dental reamer or file according to claim 1 wherein each said flange semi-circular surface is concentric to said shaft working portion longitudinal axis.

6. A dental reamer or file according to claim 1 wherein each said flange semi-circular surface is of increased radius and non-concentric to said shaft working portion longitudinal axis.

7. A dental reamer or file according to claim 1 wherein each said flange semi-circular surface is of increased radius and non-concentric to said shaft working portion longitudinal axis and wherein each said leading edge is at a negative angle relative to a plane of said longitudinal axis providing a positive cutting edge.

8. A dental reamer or file according to claim 1 wherein each said leading edge and each said trailing edge provides a cutting/scraping edge active in response to the direction of rotation of said shaft.

9. A dental reamer or file useable by reversible rotation and manipulation in a tooth root canal comprising:
- an elongated tapered shank having a rotational axis, having a proximal end portion, a distal end and a tapered working portion extending from said proximal portion to said distal end;
- the external surface of said shank working portion being defined in part by a plurality of at least two equally spaced apart continuous helical flutes formed into a central core portion of said shank working portion, each flute having a semi-circular recessed depth base surface concentric with said rotational axis and providing resistance to torque breakage, the flutes having therebetween an equal number of spiraled spaced apart flanges, each flange having in a plane perpendicular to the length of said shaft, a flange external surface having beginning and spaced apart ending edges, each edge being defined by an abrupt decrease in external surface diameter and each edge providing a cutting or scraping edge.

10. A dental reamer or file according to claim 9 wherein each said edge is at a negative angle relative to a plane of said longitudinal axis providing a positive cutting edge.

11. A dental reamer or file according to claim 9 wherein each said edge is at a positive angle relative to a plane of said longitudinal axis providing a negative scraping edge.

12. A dental reamer or file according to claim 9 wherein each said edge is at a neutral angle relative to a plane of said longitudinal axis providing a neutral cutting or scraping edge.

13. A dental reamer or file according to claim 9 having two said helical flanges, providing in planes perpendicular the length of said shaft four said edges.

* * * * *